United States Patent [19]
Lee

[11] Patent Number: 6,060,078
[45] Date of Patent: May 9, 2000

[54] CHEWABLE TABLET AND PROCESS FOR PREPARATION THEREOF

[75] Inventor: Young Won Lee, Seoul, Rep. of Korea

[73] Assignee: Sae Han Pharm Co., Ltd., Kyunggi-do, Rep. of Korea

[21] Appl. No.: 09/161,904

[22] Filed: Sep. 28, 1998

[51] Int. Cl.[7] .............................. A61K 9/20; A61K 9/28
[52] U.S. Cl. .................... 424/440; 424/439; 424/441; 424/475; 424/481; 514/777; 514/782; 514/784; 514/774; 514/785
[58] Field of Search ................... 424/440, 441, 424/439, 464, 465, 474, 475, 481

[56] References Cited

U.S. PATENT DOCUMENTS

| | | | |
|---|---|---|---|
| 4,260,596 | 4/1981 | Mackles | 424/14 |
| 4,271,142 | 6/1981 | Puglia et al. | 424/14 |
| 4,372,942 | 2/1983 | Cimiluca | 424/16 |
| 4,423,086 | 12/1983 | Devos et al. | 427/3 |
| 4,511,553 | 4/1985 | Boesig | 424/35 |
| 5,460,825 | 10/1995 | Roche et al. | 424/470 |
| 5,753,255 | 5/1998 | Chavkin et al. | 424/441 |

*Primary Examiner*—James M. Spear
*Attorney, Agent, or Firm*—Bachman & LaPointe, P.C.

[57] ABSTRACT

The present invention relates to a chewable tablet containing a medicament in a core and a process for preparation thereof. In particular, the present invention relates to a chewable tablet comprising a core containing a medicament in the center of the tablet in a state of jelly or chewable base and an outer layer wrapping the core which is made up of chewable base such as a gum, a soft candy or a caramel. The chewable tablet is easy to take and has a good taste and nice chewing property due to the unique tablet form. In addition, the tablet has an advantage in bioavailability resulting from increased absorption rate and excellent stability due to unique preparation process. Therefore, the chewable tablet and the preparation process of the present invention can be used in pharmaceutical industry usefully.

11 Claims, 1 Drawing Sheet

CHEWABLE TABLET AND PROCESS FOR PREPARATION THEREOF

FIELD OF THE INVENTION

The present invention relates to a chewable tablet containing a medicament in a core and a process for preparation thereof. In particular, the present invention relates to a chewable tablet comprising a core containing a medicament in the center of the tablet in a state of jelly or chewable base; and an outer layer wrapping the core which is made up of chewable base such as a gum, a soft candy or a caramel.

BACKGROUND OF THE INVENTION

A tablet, which has been formed by compressing a mixture of medicament and forming agent, is inconvenient to take because it must be swallowed or chewed, and troublesome especially to an aged person.

Soft tablet having good chewing property was developed, in which excipients for chewing property, elasticity and good taste were added to the medicament (Korean Patent application No. 94-2298). But, this tablet had a problem in that the medicament, an effective ingredient, was transformed in physico-chemical properties because the tablet was prepared in such severe condition as the tablet was made in a state of soft candy or jelly by mixing a medicament and forming agents and melting them at high temperatures. That is, temperature condition higher than 90° C. was required for mixing ingredients of the tablet, thus if a medicament was unstable to heat, its properties were liable to transform or the medicament itself was evaporated, which caused to deteriorate the effect of a medicament.

In addition, the conventional chewable tablet has problems to take because of sandy taste in granular chew and chalky taste in mouth.

The present inventors have successfully developed a new chewable tablet comprising a core containing a medicament in the center of the tablet in a state of jelly or chewable base; and an outer layer wrapping the core which is made up of chewable base such as a gum, a soft candy or a caramel. The tablet is easy to take and can keep the stability of a medicament. In addition, a medicament contained in the tablet can be absorbed more rapidly than that of conventional tablet.

SUMMARY OF THE INVENTION

The object of the present invention is to provide a chewable tablet that is easy to take and has a good taste and nice chewing property, and also can be useful in pharmaceutical field taking advantage of keeping the stability of a medicament and increasing bioavailability.

DETAILED DESCRIPTION OF THE INVENTION

Figure 1:
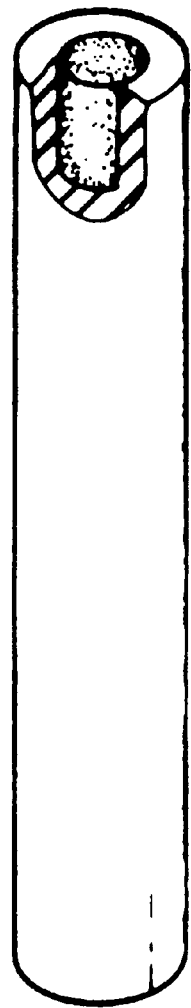
FIG. 1 is a partially sectional perspective view of a candy rope comprising a core containing a medicament in a state of jelly or chewable base; and an outer layer wrapping the core which is made up of chewable base.

In the present invention, a chewable tablet containing a medicament in a core in a state of jelly or chewable base and a process for preparation thereof are provided.

In detail, the tablet of the present invention comprises a core containing a medicament in a state of jelly or chewable base; and an outer layer of chewable base wrapping the core.

Any kind of medicament may be contained in the core, preferably a medicament of bitter taste, a medicament which is unstable to heat, vitamins which are liable to transform, natural plant extracts or other organic compounds may be contained in the core.

More preferably, vitamins such as vitamin A, vitamin B, vitamin $B_1$, vitamin $B_2$, vitamin $B_6$, vitamin C, vitamin E and vitamin K; natural plant extracts such as Sohgunjung-tang extracts, Sipchundaebo-tang extracts and *Eleutherococcus senticosus* extracts; organic compounds such as dimenhydrinate, meclazine.HCl, acetaminophen, asprin, phenylpropanolamine.HCl and cetylpyridinium chloride; or gastrointestinal agents such as aluminum hydroxide gel dried, domperidone, soluble azulene, L-glutamine and hydrotalcite may be contained in the core.

These medicaments may be used alone or in combination.

The medicament contained in the tablet may be used in usual dose.

For example, *Eleutherococcus senticosus* extracts is used in the chewable tablet in a dose of 195–390 mg/day; dimenhydrinate in a dose of 20–200 mg/day; meclazine.HCl in a dose of 25–75 mg/day; aspirin in a dose of 1–4.5 mg/day; phenylpropanolamine-HCl in a dose of 75–100 mg/day; cetylpyridinium chloride in a dose of 6–8 mg/day; and domperidone in a dose of 30–60 mg/day.

The jelly base of the core, which contains the above medicament in a state of jelly, may be selected from the group consisting of pectin, sorbitol, maltitol, isomalt, liquid glucose, sugar, citric acid and a flavoring agent.

The chewable base of the core or the outer layer may be selected from the group of gum, soft gum, soft nougat, soft candy, hard candy and caramel, which are easy to take and tasty. In addition, the chewable base may additionally contain excipients selected from the group consisting of sugars; a protecting agent of adhesion to oral cavity and crystallization of sugars; an enhancing agent of chewing property; a keeping agent of hardness and extension property; a flavoring agent; a souring agent; a coloring agent; and combinations thereof, according to the kind of chewable base.

The sugar used in the present invention may be selected from the group consisting of white sugar, liquid glucose, sorbitol, dextrose, isomalt, liquid maltitol, aspartame and lactose, and this sugar may comprise 50–90 weight % by total weight of the ingredients.

Glycerin, lecithin, hydrogenated palm oil or glyceryl monostearate may be used as a protecting agent of crystallization of the sugars in 0.04–2.0 weight % by total weight of the ingredients, to prevent adhesion to oral cavity and improve the soft property of the products.

Isomalt or liquid maltitol may be used as an enhancing agent of chewing property, which can increase the chewing properties by controlling the composition ratio and it must be prepared at temperatures of 135–140° C. under vapor pressure of 5.5 bar.

A gum such as gelatin or arabic gum may be used as a keeping agent of hardness and extension property in 0.1–2.0 weight % by total weight of the ingredients.

In addition, a flavoring agent such as a food flavor or a fruits extract; a souring agent such as citric acid may be added in adequate amount, and a coloring agent such as a food color may be optionally added in small amount.

The chewable tablet of the present invention is prepared by the process in which the medicament, an effective ingredient, is contained in the core in a state of jelly or chewable base separate from the outer layer, whereas the conventional chewable tablet was prepared by mixing a medicament and additives and then, melting them at high temperatures, therefore, forming soft candy or jelly, in which the medicament was dispersed on the whole tablet.

Figure 2:
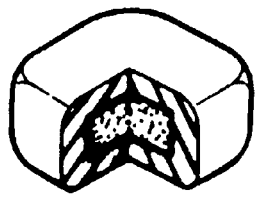
FIG. 2 is a partially sectional perspective view of a chewable tablet of the present invention made by using the candy rope of FIG. 1.

In detail, the chewable tablet of the present invention is prepared by the following process comprising the steps of:

(a) preparing an outer layer of chewable base and a core of jelly or chewable base, respectively;

(b) mixing a medicament with the jelly or chewable base of the core at room temperature (25° C.);

(c) making candy rope containing fixed amount of medicament (FIG. 1) through the process in which each of the prepared outer layer of chewable base and the core of jelly or chewable base containing medicament is put into two extruding machine, which is designed specially by the present inventors (Korean Patent application No. 98-30511), respectively, and then each of the outer layer and the core is extruded at the same time by using the above extruding machine, maintaining temperatures of 50–90° C. on the outer layer and 5–8° C. on the core; and (d) forming a chewable tablet by cutting the above candy rope (FIG. 2).

The chewable tablet prepared by the above process has an advantage in bioavailability resulting from increased absorption rate, because the tablet is dissolved or chewed in the mouth and then moved into gastrointestinal tract in a state of whole solution or granule, whereas the conventional solid tablet or capsule was absorbed through disintegration and dissolution.

Further, the conventional chewable tablet was prepared by mixing a medicament, an effective ingredient, and additives, then melting them at high temperatures as a whole, thus the medicament was liable to change in physico-chemical properties. On the contrary, the medicament contained in the chewable tablet of the present invention as an effective ingredient is not changed in physico-chemical properties and keeps the effect of medicament, therefore has a excellent stability, because the chewable tablet of the present invention is prepared by the process in which the medicament is mixed with a jelly or a chewable base at room temperature.

To confirm the stability of the chewable tablet of the present invention, an acceleration test was performed on the product prepared by the present process under certain condition ((1) room temperature, (2) 40° C., relative humidity (RH) 75%) for certain period (for 6 months, tested every 0, 2, 4, 6 months) and the changes of physico-chemical properties were observed. As a result, the chewable tablet of the present invention did not change in properties, state and content of the effective medicament and it was suitable for both of microorganism limit test and heavy metal test. The chewable tablet, therefore, has been proved to have excellent stability.

In addition, the chewable tablet of the present invention provides taste mask effect to a bitter tasty medicament, which is contained in the medicament, and better chewing property and taste than the conventional tablets by means of an outer tasty chewable base.

The present invention is further illustrated with reference to the following examples and experiment which are not intended to be in any way limiting to the scope of the invention as claimed.

EXAMPLE 1

Preparing Medicinal Chewing Gum Tablet

Dimenhydrinate, meclazine.HCl, acetaminophen, asprin or phenylpropanolamine.HCl was used for medicinal chewing gum tablet as a medicament.

| 1) medicinal chewing gum tablet with sugars | |
|---|---|
| a) gum base in one tablet | |
| gum base | 600 mg |
| lecithin | 9 mg |
| hydrogenated palm oil | 30 mg |
| liquid glucose | 700 mg |
| sorbitol solution | 70 mg |
| dextrose | 340 mg |
| sugar | 940 mg |
| aspartame | 10 mg |
| glycerin | q.s. |
| flavoring agent | q.s. |
| b) jelly base in one tablet | |
| pectin | 29 mg |
| sorbitol | 120 mg |
| liquid glucose | 220 mg |
| sugar | 400 mg |
| citric acid | q.s. |
| 2) sugar-free medicinal chewing gum tablet | |
| a) gum base in one tablet | |
| gum base | 200 mg |
| lecithin | 12 mg |
| isomalt | 415 mg |
| aspartame | q.s. |
| flavoring agent | q.s. |
| b) jelly base in one tablet | |
| pectin | 35 mg |
| sorbitol | 70 mg |
| liquid maltitol | 160 mg |
| isomalt | 430 mg |
| citric acid | q.s. |
| flavoring agent | q.s. |

EXAMPLE 2

Preparing Chewing Hard Candy Tablet

*Eleutherococcus senticosus* extracts or cetylpyridinium chloride was used for chewing hard candy tablet as a medicament.

| 1) chewing hard candy tablet with sugars | |
|---|---|
| a) candy base in one tablet | |
| sugar | 2500 mg |
| liquid glucose | 1750 mg |
| citric acid | q.s. |
| coloring agent | q.s. |
| flavoring agent | q.s. |
| b) jelly base in one tablet | |
| pectin | 29 mg |
| sorbitol | 120 mg |
| liquid glucose | 220 mg |
| sugar | 400 mg |
| citric acid | q.s. |
| 2) sugar-free chewing hard candy tablet | |
| a) candy base | |

-continued

| in one tablet | |
| --- | --- |
| isomalt | 2120 mg |
| aspartame | q.s. |
| citric acid | q.s. |
| coloring agent | q.s. |
| flavoring agent | q.s. |
| b) jelly base in one tablet | |
| pectin | 35 mg |
| sorbitol | 70 mg |
| isomalt | 160 mg |
| citric acid | 430 mg |
| flavoring agent | q.s. |

EXAMPLE 3

Preparing Chewing Soft Candy Tablet

Vitamins; a mixture of vitamins and minerals; gastrointestinal agents such as aluminum hydroxide gel dried, domperidone, soluble azulene, L-glutamine and hydrotalcite; or natural plant extracts such as Sohgunjung-tang extracts and Sipchundaebo-tang extracts was used for chewing soft candy tablet as a medicament.

| 1) chewing soft candy tablet with sugars | |
| --- | --- |
| a) candy base in one tablet | |
| sugar | 1800 mg |
| lactose | 400 mg |
| liquid glucose | 1800 mg |
| glyceryl monostearate | 20 mg |
| hydrogenated palm oil | 320 mg |
| gelatin | 8 mg |
| citric acid | q.s. |
| b) jelly base in one tablet | |
| pectin | 29 mg |
| sorbitol | 120 mg |
| liquid glucose | 220 mg |
| sugar | 400 mg |
| citric acid | q.s. |
| 2) sugar-free chewing soft candy tablet | |
| a) candy base in one tablet | |
| isomalt | 1800 mg |
| liquid matitol | 1900 mg |
| arabic gum | 150 mg |
| lecithin | 240 mg |
| citric acid | q.s. |
| coloring agent | q.s. |
| flavoring agent | q.s. |
| b) jelly base in one tablet | |
| pectin | 35 mg |
| sorbitol | 70 mg |
| liquid maltitol | 160 mg |
| isomalt | 430 mg |
| citric acid | q.s. |
| flavoring agent | q.s. |

EXPERIMENT

Stability test

The tablet of the present invention was examined on the stability by means of the following. The tests such as appearance, microorganism limit, heavy metal and content were carried out under the condition of 40° C. and 75% RH for 6 months, and the result was shown in table 1.

In addition, the above tests were carried out under the condition of room temperature (25° C.) for 6 months, and the result was shown in table 2.

TABLE 1

Results under the condition of 40° C. and 75% RH

| | Time | | | |
| --- | --- | --- | --- | --- |
| Test | At base (0 month) | After 2 months | After 4 months | After 6 months |
| Appearance | Suitable | Suitable | Suitable | Suitable |
| Microorganism limit | Suitable | Suitable | Suitable | Suitable |
| Heavy metal | Suitable | Suitable | Suitable | Suitable |
| Content (%) | 112.74 | 112.70 | 112.65 | 112.54 |

TABLE 2

Results under the condition of room temperature (25° C.)

| | Time | | | |
| --- | --- | --- | --- | --- |
| Test | At base (0 month) | After 2 months | After 4 months | After 6 months |
| Appearance | Suitable | Suitable | Suitable | Suitable |
| Microorganism limit | Suitable | Suitable | Suitable | Suitable |
| Heavy metal | Suitable | Suitable | Suitable | Suitable |
| Content (%) | 112.74 | 111.96 | 111.96 | 111.94 |

As shown in the above, the chewable tablet of the present invention did not change in appearance, and the content of the medicament, and it was suitable for both of microorganism limit test and heavy metal test. The chewable tablet, therefore, has been proved to be stable in the process of circulation.

EFFECT OF THE INVENTION

As described distinctly in the above, the present invention provides the chewable tablet which has an advantage in bioavailability resulting from increased absorption rate, because it is dissolved or chewed in the mouth and then moved into gastrointestinal tract in a state of whole solution or granule. And the medicament contained in the chewable tablet of the present invention as an effective ingredient is not changed in physico-chemical properties and keeps the effect of medicament due to the unique preparation process.

In addition, the chewable tablet containing even a bitter tasty medicament can be taken by dissolving or chewing because of good taste and flavor, and the tablet is easy to carry and can be taken whenever and wherever without water, as well.

What is claimed is:

1. A chewable tablet comprising a core containing a medicament in a state of jelly or chewable base; and an outer layer of chewable base wrapping the core, wherein the said chewable base contains an enhancing agent of chewing property selected from the group consisting of isomalt and liquid maltitol and a keeping agent of hardness and extension property being a gum including gelatin or arabic gum.

2. The chewable tablet of claim 1 wherein said jelly base of the core is selected from the group consisting of pectin, sorbitol, maltitol, isomalt, liquid glucose, sugar, citric acid and flavoring agent.

3. The chewable tablet of claim 1 wherein said chewable base of the core or the outer layer is selected from the group consisting of gum, soft gum, soft nougat, soft candy, hard candy and caramel.

4. The chewable tablet of claim 3 wherein the tablet additionally contains excipients selected from the group consisting of sugars; a protecting agent of adhesion to oral cavity and crystallization of sugars; a flavoring agent; a souring agent; a coloring agent; and combinations thereof, according to the chewable base.

5. The chewable tablet of claim 4 wherein said sugar is selected from the group consisting of white sugar, liquid glucose, sorbitol, dextrose, isomalt, liquid maltitol, aspartame and lactose.

6. The chewable tablet of claim 4 wherein said protecting agent of adhesion to oral cavity and crystallization of sugars is selected from the group consisting of glycerin, lecithin, hydrogenated palm oil and glyceryl monostearate.

7. The chewable tablet of claim 1 wherein said keeping agent of hardness and extension property comprises 0.1–2.0 weight % by total weight of the ingredients.

8. The chewable tablet of claim 1 wherein said enhancing agent of chewing property is prepared at temperatures of 135–140° C. and under vapor pressure of 5.5 bar.

9. The chewable tablet of claim 1 wherein said medicament, which is contained in the core, is vitamins selected from the group consisting of vitamin A, vitamin B, vitamin $B_1$, vitamin $B_2$, vitamin $B_6$, vitamin C, vitamin E and vitamin K; natural plant extracts selected from the group consisting of Sohgunjung-tang extracts, Sipchundaebo-tang extracts and *Eleutherococcus senticosus* extracts; organic compounds selected from the group consisting of dimenhydrinate, meclazine.HCl, acetaminophen, aspirin, phenylpropanolamine.HCl and cetylpyridinium chloride; or gastrointestinal agents selected from the group consisting of aluminum hydroxide gel dried, domperidone, soluble azulene, L-glutamine and hydrotalcite.

10. The chewable tablet of claim 4 wherein said sugar comprises 50–90 weight % by total weight of the ingredients.

11. The chewable tablet of claim 4 wherein said protecting agent of adhesion to oral cavity and crystallization of sugars comprises 0.04–2.0 weight % by total weight of the ingredients.

* * * * *